United States Patent [19]
Tomlinson et al.

[11] Patent Number: 5,783,202
[45] Date of Patent: Jul. 21, 1998

[54] PEDICULICIDAL MOUSSE COMPOSITION FOR KILLING HEAD LICE

[75] Inventors: Roderick P. Tomlinson, Rowville; Neil G. Halls, Glen Waverley; Albert Z. Abram, Rowville, all of Australia

[73] Assignee: Soltec Research Pty. Ltd., Rowville, Australia

[21] Appl. No.: 403,110

[22] Filed: Mar. 14, 1995

[51] Int. Cl.$^6$ ..................................................... A61K 9/12
[52] U.S. Cl. ................... 424/405; 424/45; 424/DIG. 10; 514/919; 514/937; 514/945
[58] Field of Search ................... 424/405, DIG. 10, 424/43, 45; 514/937, 919, 945

[56] References Cited

U.S. PATENT DOCUMENTS

| | | | |
|---|---|---|---|
| 3,131,153 | 4/1964 | Klausner | 514/945 |
| 3,159,535 | 12/1964 | Sesso et al. | 424/45 |
| 4,822,613 | 4/1989 | Rodero | 424/405 |
| 4,923,897 | 5/1990 | Flashinski | 514/531 |
| 4,981,678 | 1/1991 | Tomlinson | 424/45 |
| 5,094,853 | 3/1992 | Hagarty | 424/405 |
| 5,516,504 | 5/1996 | Tomlinson | 424/45 |

FOREIGN PATENT DOCUMENTS

| | | |
|---|---|---|
| 2060594 | 2/1991 | Canada . |
| 0 125 471 A2 | 11/1984 | European Pat. Off. . |
| 0 566 495 A1 | 10/1993 | European Pat. Off. . |

OTHER PUBLICATIONS

Taplin, D., Meinking, T.L., Castillero, P.M., Sanchez, R., Permethrin 1% creme rinse for the treatment for *Pediculus humanus var. capinis* infestation, *Pediatr. Dermatol.* 3:344–348 (1986).

Burgess, L. *Malathion lotions for head lice a less reliable treatment than commonly believed. Pharm. J.* 247:630–632 (1991).

Burgess, I., *Carbaryl Lotions for Head Lice —New Laboratory Tests Show Variations in Efficiency, Pharm. J.*, 245:159–161 (1990).

Burgess, I., *Malathion Lotions for Head Lice —A Less Reliable Treatment than Commonly Believed, Pharm. J.*, 247:630–632 (1991).

Burgess, I., Veal, L., Sindle, T., *The Efficacy of d-Phenothrin and Permethrin Formulations Against Headlice: A Comparison, Pharm. J.*, 249:692–693 (1992).

Armitage, P., Berry, G., *Statistical Methods in Medical Research*, 2nd ed., Oxford Blackwell Scientific Publications, 115–120 (1987).

*Clinical Therapeutics*, vol. 16, No. 1, pp. 58–64 (1994).

*Primary Examiner*—Raj Bawa
*Attorney, Agent, or Firm*—Synnestvedt & Lechner

[57] ABSTRACT

A non-residual, pediculicidal mousse composition for treating head lice consisting essentially of about 0.1 to about 10% w/w of pediculicidal agent, about 70 to about 97% w/w of a foaming agent, which includes water, a surface active agent, a fatty alcohol and a surface active agent, and about 3 to about 20% w/w of an aerosol propellant. In one aspect of the invention, the pediculicidal agent and the foaming agent of the foregoing composition act synergistically against head lice and their eggs.

29 Claims, 1 Drawing Sheet

PEDICULICIDAL MOUSSE COMPOSITION FOR KILLING HEAD LICE

BACKGROUND OF THE INVENTION

The present invention relates to compositions particularly suitable for the treatment of human head lice, *Pediculus humanus capitis*, but is also applicable to other types of lice such as clothing lice, *Pediculus humanus humanus*.

Head lice persist in developed countries, as well as in underdeveloped countries despite the availability of modern chemical insecticide treatments, public health education, and community based programs of lice eradication. The reason for this persistence is a combination of factors. Some lice control programs suffer logistical problems. Additionally, some chemical treatments are not entirely effective, particularly shampoo formulations which continue to retain their widespread popularity.

A shampoo will fail for several reasons, but most significant among these is the large dilution factor which occurs during use. Depending on how oily the hair is, the average head of hair will take between 90–150 mls of water to be thoroughly wetted. Even in hard water areas approximately 5 ml of shampoo is required to work up a good lather, a dilution of 1:30. If the water is soft, the dilution factor could be higher than 1:150.

Many commonly used pediculicidal compositions rely on residual action on the hair by the pesticide after the application of the composition to the patient. Permethrin creme rinses are applied after shampooing and rely on the residual action of the insecticide on the hair after the shampoo treatment as noted by Taplin et al. (Taplin, D., Meinking, T. L., Castillero, P. M., Sanchez, R., *Permethrin 1% creme rinse for the treatment of Pediculus humanus var. capinis infestation, Pediatr. Dermatol.* 3: 344–348 (1986)). However, despite the convenience of residually active insecticides, such as permethrin, for some consumers, the effect may be inconsistent in development or reduced by environmental conditions resulting in treatment failures demonstrated by the emergence of the eggs after treatment. In addition, because these creme rinses are applied after shampooing, many of the lice are not dislodged from their reflex action of grasping the hairs. Dead lice may only be found during subsequent washing or grooming.

There are other limitations associated with residual action pediculicidal formulations. The weakness of such treatments is usually inadequately explained in product literature written for customers, leading them to believe it will give total protection from reinfection or hatching of eggs. The product monograph for one particular type of creme rinse marketed in the U.K. as Lyclear® notes the emergence of nymphs but stipulates that they will subsequently die from exposure to residual insecticide. This information does not appear in the product inset in any country in which the product is marketed. Therefore most consumers automatically assume that the product has failed and re-treat with insecticide if they find hatchlings within a few days after treatment, resulting in potential overuse and toxic use of insecticide.

The second disadvantage of this type of pediculicidal treatment is that as residual activity wears off, there will be a point beyond which any lice invading the head will not be killed by lower insecticidal levels. It is postulated that such conditions can lead to resistant strains of lice. Non-residual insecticides are less likely to induce resistance. They also permit users the opportunity to trace the source of the infection, which ultimately gives a better chance of eliminating the infection.

Natural pyrethrins are used as pediculicides worldwide and demonstrate a good safety level. However, although pyrethrins are the most common ingredients in anti-lice products, most of these compositions are shampoos which, due to their presentation as discussed above, show minimal activity against louse eggs. (Burgess, L. *Malathion lotions for head lice a less reliable treatment than commonly believed. Pharm. J.* 247: 630–632 (1991)) Natural pyrethrins have long ben successful as insecticides because they rapidly incapacitate insects, an effect known as "knockdown". Provided that sufficient material is present, the knockdown effect persists to the eventual death of the insect. The lethal effect of pyrethrins is normally synergized by adding piperonyl butoxide to incapacitate the enzymes that would otherwise detoxify the pyrethrins.

However, the rapid penetration and action of pyrethrins on lice can be hindered if they are exposed to water. Lice which come in contact with water grasp hairs reflexively and close their breathing spiracles to avoid being drowned. Since insecticides are effective only because of their entry into the creature via the spiracles, when these spiracles are closed, the chances of the insecticide penetrating the insect when the creature is first, or simultaneously, exposed to water is negligible, especially if the formulation is a shampoo rather than a residual action rinse. Thus, pyrethrin shampoos which are designed to be administered to an infested patient after wetting of the hair, may not kill lice consistently (Burgess, L. unpublished data, 1991). Pyrethrins are thus widely regarded as being nonovicidal.

When it comes to eggs, an insecticide needs to make its way through a physical system that is designed to keep out a wide variety of chemical materials and keep water in. The egg shell has a detachable cap that bears a number of air pores that act effectively to exclude fluids but will allow the passage of gases, and it is through these pores that the developing embryo breathes. However, it is also through these pores that suitable formulations can penetrate. The problems of penetration are dependent on physical parameters.

Generally, the more viscous a fluid is, and the greater the surface tension, the less chance of penetration of the pores. However, even alcoholic solutions, which have the advantage of a low wetting angle that should allow fluid to flow into the pores, are not free of problems because they can develop air bubbles that are larger than the pores and that subsequently hinder penetration to the chorionic membrane of the egg.

Aqueous lotions, cream rinses and shampoos have too great a wetting angle for fluid to flow into the pores directly, and will only enter if appropriate excipients are included that will wet and flow more readily than the body of the formulation. Consequently, despite the bubbles of a shampoo's foam being small enough to enter the pores, they are inhibited by the aqueous medium.

The patent literature discloses several attempts to address the problem of human head lice.

European patent application 566495-A1 to FABRE SANTE PIERRE discloses a composition comprising a synergistic combination of at least one pyrethroid and crotamiton together with various excipients. The composition is said to avoid resistance problems and to have a good efficacy/toxicity ratio.

Canadian patent application 2060594 discloses a licicidal and ovicidal composition in which the active ingredient is limonene. It is pertinent to note here that in certain countries only particular active agents have regulatory approval as medical treatments. Thus, the composition described in this patent may not be available for sale in all countries.

European patent 125471 to Wellcome Foundation Ltd and Coopers South Africa Pty Ltd describes a foaming pesticide comprising a synthetic pyrethroid or organophosphate in a form that will break in 2–20 seconds for deposit of the active agent on an animal to be treated. This formulation is limited to the extent that the foam may in fact break down too quickly to enable its application in an efficient manner, thereby risking exposure of ears and eyes to the potentially toxic active.

In view of the difficulties outlined above, it is an object of this invention to provide an effective pediculicidal composition for treatment of lice infestations, particularly head lice infestations. Such compositions must be non-toxic and logistically easy to administer to a patient; they also should result in lice eradication in a minimum number of treatments, preferably only one.

DESCRIPTION OF THE INVENTION

Figure 1:
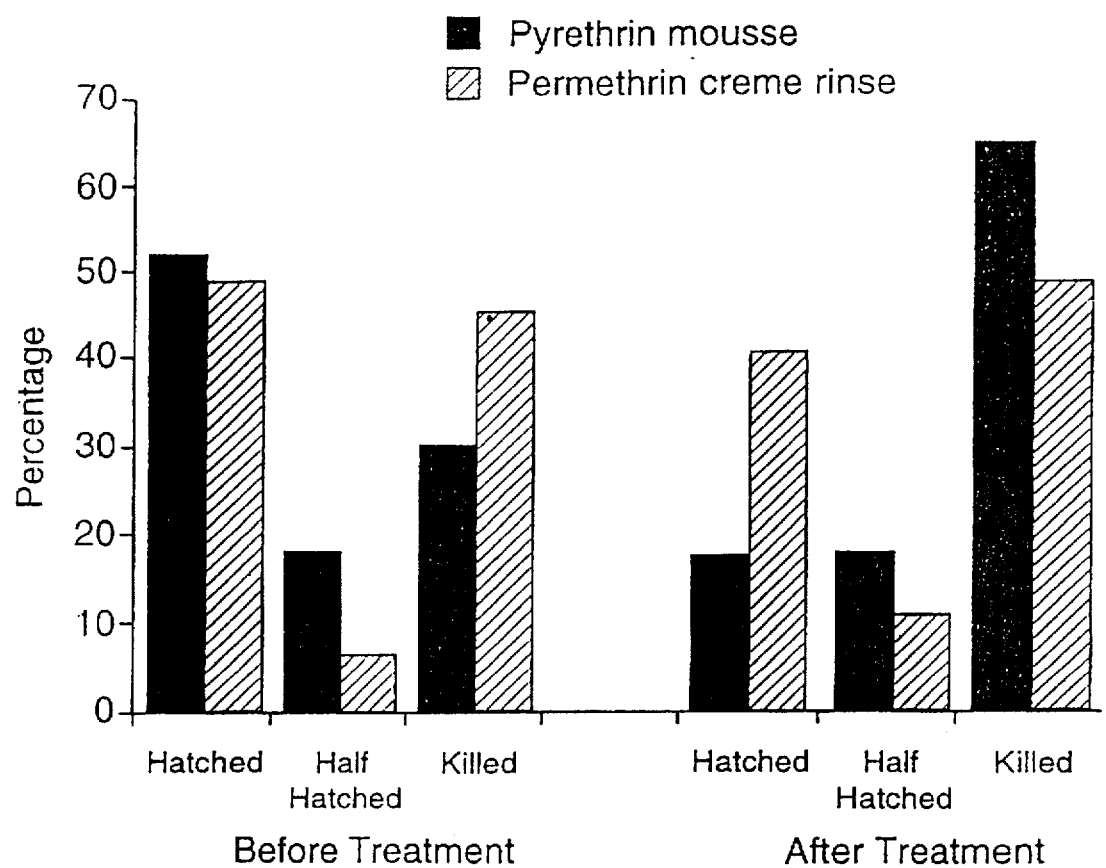
FIG. 1 is a graph comparing the hatching and mortality of louse eggs removed from patients (treated with either pyrethrin mousse in accordance with the invention or a prior art permethrin creme rinse) before and after treatment.

To this end there is provided an improved pediculicidal composition containing a pediculicidal agent in an aerosolized mousse form which is easy and safe to use. In particular, the invention relates to a pediculicidal composition containing a) from about 0.1 to about 10% w/w of a pediculicidal agent, preferably, pyrethrin, and, optionally from about 0.5 to about 15% w/w of a synergizer therefor, such as piperonyl butoxide, b) about 70 to about 97% w/w of a foaming agent, which is preferably a quick breaking alcoholic foaming agent; and c) from about 3 to about 20% w/w of an aerosol propellant.

In the practice of this invention, it has been found that the activity of the pyrethrin pediculicidal agent in the composition is enhanced by the action of the foaming agent, resulting in a higher kill rate, particularly against louse eggs, than can be expected by the use of the pyrethrin alone. Furthermore, the non-active, carrier portion of the formulation of the invention, it has been found, is lousicidal of itself without there being any reliance on residual insecticidal activity of the pediculicide, as is the usual mode of action of other popular insecticides. It is thereby possible to effect complete clearance of the infestation of lice in a single treatment, thus exposing the patient to a lower level of pesticides, and providing a better opportunity to trace the source of the infestation, the only certain means of avoiding reinfestation. In vitro experimental work shows that pyrethrins in a foaming alcohol-based vehicle can penetrate the aerophyle breathing pores of the louse egg shell cap by forming quick breaking bubbles of a size close to the size of the pores, with a rate of deposition sufficient to generate ovicidal and insecticidal activity equal to or better than the best pediculicidal formulations currently available. Thus, in one aspect, the present invention provides a pediculicidal foam aerosol composition as described above wherein the pediculicidal agent and the foaming agent act synergistically in the eradication of lice infestation.

Preferred Features of the Invention

The insecticide, preferably pyrethrin, is carried by a foaming agent in the compositions of the present invention, more particularly of a quick breaking foam variety. This has the ability to provide a thick ball of foam carrier for the pyrethrin, which can easily be transported by the user from, say, the palm of the hand, to the head, whereupon it disintegrates quickly when spread and massaged into the hair. Thus, proper coverage of the hair to be treated can be effected without first wetting the hair and without spillage of the composition.

In accordance with the invention, the pediculicidal composition preferably contains:

a) from about 0.1 to about 10% w/w of an active pediculicide and, optionally, from about 0.5 to about 15% w/w of a synergizer therefor;

b) about 70 to about 97% w/w of a foaming agent comprising
  (i) an aliphatic alcohol,
  (ii) a fatty alcohol,
  (iii) water,
  (iv) a surface active agent; and (c) from about 3 to about 20% w/w of an aerosol propellant.

Preferably, the active pediculicide according to the invention is one or more of the pyrethrins, and the preferred synergizer therefor is piperonyl butoxide.

Desirably, the formulations according to the invention comprise from about 0.1 to about 5.0% w/w pyrethrin (50% w/w) and from about 1 to about 8% w/w piperonyl butoxide (90% w/w).

Preferably, the compositions according to the invention contain from about 0.1 to about 1.0% w/w pyrethrins (50% w/w) and from about 1 to about 5% w/w piperonyl butoxide (90% w/w). In one presently preferred composition according to the invention, the pyrethrin is present in an amount of about 0.666% w/w (50% w/w) and the piperonyl butoxide is present in an amount of about 4.4% w/w (90% w/w). In another preferred embodiment, the amount of pyrethrin is about 0.165% w/w and the piperonyl butoxide is present in an amount of about 1.65% w/w.

The aliphatic alcohol, for example, methyl alcohol, ethyl alcohol, isopropyl alcohol, butyl alcohol, propylene glycol or mixtures thereof, is used in amounts from about 20 to about 60% w/w of the foaming agent, more preferably from about 25 to about 50% w/w.

Water is used in amounts from about 30 to about 80% w/w, preferably from about 50 to about 70% w/w, of the foaming agent.

The fatty alcohol, for example, cetyl alcohol, stearyl alcohol, lauryl alcohol, myristyl alcohol, palmityl alcohol or mixtures thereof, is present preferably in amounts of from about 0.5 to about 7.5% w/w, more preferably from about 1 to about 3% w/w of the foaming agent. A preferred fatty alcohol is a nonionic emulsifying wax known as Polawax GP200 (Croda Chemicals Ltd.) which is a synergistic blend of selected fatty alcohols with nonionic surface active materials.

The surface active agent is preferably an ethoxylated surface active agent selected from ethoxylated sorbitan esters such as ethyoxylated sorbitan stearate or palmitate, oleates, nonyl phenol ethoxylates, fatty alcohol ethoxylates (as an emulsifier) and quaternary ammonium phosphate salts, typically in amounts of from about 0.5 to about 9.5% w/w of the foaming agent. Preferably used is an oxyethylalkylammonium phosphate known as Dehyquart SP (Henkel) or Quaternium 52 (CTFA). Quaternium 52 can also behave as a corrosion inhibitor, which is desirable in the presence of corrosive substances such as surfactants, in this case the Polawax GP200.

Care should be taken to select a propellant most compatible to the entire system. In this respect, the propellant is preferably selected from the group consisting of propane, butane, dichlorodifluoromethane, dichlorotetrafluoroethane, and octafluorocyclobutane. As mentioned, the propellant should be present in amounts of from about 3 to about 20% w/w, preferably from about 5 to about 15% w/w.

Preferred compositions according to the invention thus contain:

| Component | % w/w |
|---|---|
| Water, Purified | 35.0–60.0 |
| Propylene Glycol | 0.5–5.0 |
| Polawax GP200 | 0.5–5.0 |
| Quaternium-52 | 0.5–5.0 |
| Pyrethrins I and II (50% w/w) | 0.1–5.0 |
| Piperonyl Butoxide (90% w/w) | 0.1–8.0 |
| Ethanol | 20.0–40.0 |
| Propane/Butane | 3.0–20.0 |

To prevent the tendency of the pediculicidal composition to dry out the skin of the scalp of the patient, an emollient may be incorporated into the composition.

Emollients which are particularly preferred are lanolin and polyols such as glycerol, propylene glycol, sorbitol and low molecular weight polymers thereof. Other examples of emollients are vinyl alcohols and polyvinyl pyrrolidone.

A typical formulation of the present invention is as follows:

| Component | % w/w |
|---|---|
| 1. Water, Purified | 52.373 |
| 2. Propylene Glycol | 2.000 |
| 3. Polawax GP200 | 1.500 |
| 4. Quaternium-52 | 1.000 |
| 5. Pyrethrins I and II (50% w/w) | 0.665 |
| 6. Piperonyl Butoxide (90% w/w) | 4.233 |
| 7. Ethanol | 26.729 |
| 8. Propane/Butane | 11.500 |
| | 100.000 |

An alternative typical formulation is:

| Component | % w/w |
|---|---|
| 1. Water, Purified | 58.784 |
| 2. Propylene Glycol | 2.000 |
| 3. Polawax GP200 | 1.000 |
| 4. Quaternium-52 | 1.000 |
| 5. Pyrethrins I and II (50% w/w) | 0.346 |
| 6. Piperonyl Butoxide (90% w/w) | 1.870 |
| 7. Ethanol | 30.000 |
| 8. Propane/Butane | 5.000 |
| | 100.000 |

It should be noted that the governmental regulations of certain countries may place limits on the amount of active agents to be included in head lice formulations.

EXAMPLES

Example 1

Comparative trials were conducted as follows to compare the effectiveness against human head lice of a mousse/foam aerosol composition in the absence of an active ingredient, with that of mousse/foam aerosol portion of the composition of the invention, containing the active ingredient itself. The results establish the synergism between the mousse/foam aerosol portion of the compositions of the invention and the active, pediculicidal ingredient.

A composition of the present invention was tested against an ungassed composition containing no pyrethrums, no piperonyl butoxide and no propellant and against a second sample comprising mousse/foam aerosol composition containing no pyrethrums and no piperonyl butoxide. The formulations tested are set forth in Table 1. A control product constituting a conventional shampoo was also used.

TABLE 1

| | (% w/w) | | |
|---|---|---|---|
| | Formulation according to invention | Mousse Vehicle E40/61/1 | Ungassed Vehicle E40/61/1 |
| Water Purified | 58.784 | 61.000 | 64.22 |
| Propylene Glycol | 2.000 | 2.000 | 2.10 |
| Emulsifying Wax | 1.000 | 1.000 | 1.05 |
| Quaternium-52 | 1.000 | 1.000 | 1.05 |
| Pyrethrins I & II | 0.346 | — | — |
| Piperonyl Butoxide | 1.870 | — | — |
| Ethanol | 30.000 | 30.000 | 31.58 |
| Propane/Butane | 5.000 | 5.000 | — |

The results of the tests are seen in Tables 2 and 3. It is evident that while the mousse vehicle is not 100% effective in achieving mortality of adult lice or eggs, it nevertheless has a greater mortality effect than the ungassed vehicle. Thus the effectiveness of the active ingredient alone is augmented.

TABLE 2

Effect on Adult Lice

| | | Number of Lice | | | Mortality |
|---|---|---|---|---|---|
| Treatment | Replicate | Total | Moribund | Killed | % |
| Formulation according to the invention | 1 | 20 | 7 | 13 | |
| | 2 | 20 | 0 | 20 | 100 |
| | 3 | 20 | 0 | 20 | |
| Mousse vehicle batch E40/61/1 | 1 | 20 | 2 | 8 | |
| | 2 | 20 | 7 | 7 | 52.5 |
| | 3 | 21 | 4 | 4 | |
| Ungassed vehicle batch E40/61/1 | 1 | 20 | 0 | 5 | |
| | 2 | 20 | 1 | 1 | 16.7 |
| | 3 | 20 | 0 | 3 | |
| Control | 1 | 20 | 0 | 0 | |
| | 2 | 21 | 1 | 1 | 4.9 |
| | 3 | 20 | 0 | 1 | |

TABLE 3

Effect on Louse Eggs

| | | No. of Lice | | | |
|---|---|---|---|---|---|
| Treatment | Replicate | Total | Hatched | Half-Hatched | Mortality %* |
| Formulation according | 1 | 239 | 2 | 5 | |
| | 2 | 197 | 2 | 6 | 98.5 |
| | 3 | 129 | 4 | 4 | |

TABLE 3-continued

Effect on Louse Eggs

| Treatment | Replicate | No. of Lice Total | Hatched | Half-Hatched | Mortality %* |
|---|---|---|---|---|---|
| to the invention Mousse vehicle batch E40/61/1 | 1 2 3 | 146 312 70 | 128 254 54 | 3 11 1 | 10.6 |
| Ungassed vehicle batch E40/61/1 | 1 2 3 | 215 145 197 | 173 124 175 | 6 4 7 | 8.3 |
| Control | 1 2 3 | 223 254 138 | 208 239 121 | 2 4 3 | 7.6** |

*Percentage mortality adjusted using Abbott's correction for control mortality.
**Actual mortality of control group.

Example 2

This example describes field and laboratory studies of the efficacy of a pyrethrin mousse containing 0.165% pyrethrins and 1.65% piperonyl butoxide in a quick breaking foam base compared with a permethrin creme rinse sold under the trademark Nix Creme Rinse (Wellcome Australia Limited).

Laboratory Study

Tests against laboratory colony lice and their eggs were performed as described in Burgess, L. Carbaryl Lotions for Head Lice—New Laboratory Tests Show Variations in Efficiency, Pharm. J., 245: 159–161 (1990), Burgess, L., Malathion Lotions for Head Lice—A Less Reliable Treatment than Commonly Believed, Pharm. J., 247: 630–632 (1991), and Burgess, L., Veal, L., Sindle, T., The Efficacy of d-Phenothrin and Permethrin Formulations Against Headlice: A Comparison, Pharm. J., 249: 692–693 (1992). Young adult and third instar nymphal lice and eggs up to 48 hours old, from the Cambridge reference strain culture colony of clothing lice, Pediculus humanus humanus, were laid on nylon gauze. Because the intended mode of use is different for each of the two products, the laboratory test protocols were designed to mimic use by patients. Lice and eggs were treated with pyrethrin mousse by dipping them into the expressed foam, spreading it over the substrate with a fingertip, and washing the mousse off after 10 minutes using a 1:15 mixture of balanced pH shampoo (Timotei, Chesebrough Pond's Inc., Greenwich, Conn.) and water. Those treated with permethrin creme rinse were washed with a pH-balanced shampoo before the product was applied and then subsequently rinsed off with water. Control groups of lice and eggs were prepared concurrently and exposed to a 1:15 pH-balanced shampoo only. Pediculicidal effects were assessed after 18 hours. Ovicidal activity was assessed after 14 days of incubation, at 30°±2° C. and 50% relative humidity, by which time the control batches of eggs had completed hatching.

Field Study

The field evaluation of pyrethrin mousse was performed as part of a wider project during January to March 1993, in Dhaka, Bangladesh. Permission to import the materials was obtained from the Bangladesh Drug Regulatory Authority. Ethical approval and clinical supervision were arranged via the Metropolitan Medical Center, Mohakali, Dhaka.

The trial was conducted at two centers. Forty-four children between the ages of 7 and 15 years and eight adults with active head lice infections, identified by the presence of live lice, were enrolled. A prevalence of 75% lice infection was identified at a school and 100% at a child's home. Active infections were identified by combing through potential patients' hair with a polycarbonate detection comb. (The smallest, newly hatched nymphal stages of lice are able to be removed with these combs.) Those patients with both live lice and eggs present in the hair were admitted to the trial. In addition to informed consent granted by the head teacher and home superintendent, in loco parentis, all patients were given written and verbal explanations of the study purpose in their own language, and informed consent was obtained from a responsible person as designated or appropriate.

After each patient was admitted to the trial, an attempt was made to remove five eggs still attached to hairs from the scalp. It was not possible, however, to find five eggs on every patient. A maximum of 50 eggs were seen, but the majority were already hatched, so only a few viable eggs could be obtained from each patient. In some cases, fewer than six viable eggs were found, probably due to the regular grooming and nit removal procedures performed by most families in Bangladesh.

Treatments were distributed randomly and applied by one of the investigators in accordance with the manufacturers' instructions. (A 10-minute treatment time was required for both products.) The pyrethrin mousse was applied to dry hair by distributing the foam along partings or inserting the applicator nozzle under the hair and expressing a quantity of foam that was then massaged into the hair and over the scalp with the fingers. After the 10-minute treatment period, the pyrethrin mousse was washed off by another investigator using a pH-balanced shampoo. Those treated with permethrin creme rinse were shampooed with a pH-balanced shampoo and towel-dried before treatment, then administered the formulation, which was massaged into the hair and spread evenly with a grooming comb. At the end of the 10-minute treatment time, the permethrin creme rinse was washed off using plain tap water.

After removal of the pediculicide, each patient was re-examined to ensure that no live lice were present. An additional batch of five eggs was removed at this time if possible. The pre- and post-treatment eggs for each patient were enclosed in individually marked containers and incubated until the nymphs had completed hatching. Hatching was evaluated microscopically by an investigator unaware of which treatment had been used.

Following treatment, all patients were examined on at least two occasions on alternate days, up to 8 days post-treatment; some were examined on day 14. These examinations were performed by visual inspection and by drawing a polycarbonate detection comb through the hair several times over each sector of the scalp.

Eradication of lice infections in the field study was evaluated using the binomial test (Armitage, P., Berry, G., Statistical Methods in Medical Research, 2nd ed., Oxford Blackwell Scientific Publications, 117–120 (1987)) to compare treatments at each assessment point. The same analysis was used to compare the results of incubation of eggs from pre- and post-treatment specimens.

Evaluation of laboratory tests was made by Poisson approximation.

Results

Laboratory Study

Both formulations produced toxic signs in lice within a few minutes of drying after the final wash. When assessed 16 hours later, all lice in both groups had been killed (Table 4), although 35% of the permethrin-treated lice and 78% of the pyrethrin-treated lice still exhibited limb tremors.

When tested against louse eggs, however, pyrethrin mousse performed significantly better in preventing the emergence of nymphs from their egg shells (Z=8.38, P<0.001) and at stopping their development before they were able to lift the egg shell cap prior to emergence, recorded as half-hatched in Table II (Z=7.67, P<0.001). Neither of the nymphs from pyrethrin mousse-treated eggs that completed its emergence was alive when discovered. Most of the nymphs that emerged from permethrin-treated eggs continued to move for some time; however, these lice were intoxicated with insecticide and mostly unable to feed.

Field Study

Head louse eggs take 6 to 7 days to hatch; therefore, any eggs that survived treatment on day 0 would be expected to have hatched by day 6. Nymphal lice emerging during this period could, at most, reach the second instar development stage. Any lice found in the third nymphal instar or as adults could only be new, fresh lice from infected contacts.

By day 6, 19 pyrethrin mousse-treated patients were available for assessment; other patients were unavailable for assessment. Two girls treated with pyrethrin mousse were identified on day 6 as having been reinfected from contacts. Two adult female lice were removed from one patient; the other patient was found to have three third instar nymphs. Such reinfections were anticipated because no residual insecticide activity exists for pyrethrin mousse (Table 6).

Only one patient in the pyrethrin group was found to have any newly emerged nymphs (identified on day 4). Both lice were moribund and had apparently been intoxicated with insecticide as they emerged from the egg shell.

None of those patients examined after permethrin treatment were found to have lice.

No adverse reaction to either treatment was observed by the investigators or reported by the patients.

After discounting empty egg shells inadvertently removed, 127 eggs were obtained in both pre- and post-treatment groups from the 27 pyrethrin-treated patients, who had at least 5 eggs. The permethrin group of 10 subjects provided 33 eggs before treatment and 37 after treatment.

TABLE 4

Efficacy of Treatments Against Clothing Lice In Vitro

| Formulation | No. of Lice | Mortality (%) |
|---|---|---|
| Pyrethrin mousse | 100 | 100 |
| Permethrin creme rinse | 100 | 100 |
| Control | 100 | 5 |

TABLE 5

Efficacy of Treatments Against Louse Eggs In Vitro

| Formulation | Number of Eggs | | | Mortality* (% ± SD) |
|---|---|---|---|---|
| | Total | Hatched | Half-Hatched | |
| Pyrethrin mousse | 1887 | 2 | 3 | 99.9 ± 0.3 |
| Permethrin creme rinse | 1701 | 67 | 59 | 95.3 ± 5.8 |
| Control | 989 | 802 | 25 | 19.3 ± 6.5 |

This series of tests consisted of 21 replicates conducted in three groups over a period of 8 weeks.
*Percent mortality adjusted using Abbott's correction for control mortality.

TABLE 6

Efficacy of Treatment Measured as Patients Free of Lice (number/total seen)

| | 0 | 2 | 4 | 6 | 8 | 14 |
|---|---|---|---|---|---|---|
| Pyrethrin mousse | 42/42 | 39/39 | 23/24* | 17/19** | 5/5 | 4/4 |
| Permethrin creme rinse | 10/10 | 8/8 | 8/8 | 3/3 | 2/2 | NA |

NA = not available
*Two moribund newly hatched nymphs found on one patient
**Two patients reinfected from contacts At the end of incubation, 52% of eggs removed prior to pyrethrin mousse treatment hatched successfully, which is statistically indistinguishable from the 48.5% found in the equivalent permethrin creme rinse group (FIG. 1). After treatment, however, the number of hatchlings in the pyrethrin mousse group was reduced to 17.8%, compared to 40.5% for the permethrin creme rinse group. There was also a significant increase in dead embryos from 29.9% to 64.3% for the pyrethrin group (P<0.001), whereas the increase in the permethrin group (from 45.5% to 48.6%) was insignificant. Overall, use of pyrethrin mousse was more effective at preventing hatching of eggs than permethrin creme rinse (P<0.001).

The results of the field tests confirm the high level of pediculicidal and, more importantly, ovicidal activity identified in in vitro tests. Because the pyrethrin mousse is capable of eradicating an infestation with a single treatment, without depending on residual insecticidal activity, it offers the patient a lower level of exposure to harmful pesticides and the opportunity to trace and eradicate the source of the infection. Since eradication is the only certain means of avoiding reinfection, the quick breaking lousicidal compositions of the invention can be considered to be more effective than alternate lousicidal treatments currently on the market. In this context, synergized pyrethrin mousse in accordance with the invention is a novel development in the treatment of head lice that should satisfy the convenience, safety and efficacy requirements of consumers and professionals alike.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A pediculicidal mousse composition consisting essentially of:

| Ingredient | % w/w |
| --- | --- |
| Water, Purified | from about 35 to about 60 |
| Propylene Glycol | from about 0.5 to about 5 |
| Nonionic Emulsifying Wax | from about 0.5 to about 5 |
| Quaternium-52 | from about 0.5 to about 5 |
| Pyrethrins I and II | from about 0.1 to about 5 |
| Piperonyl Butoxide | from about 1 to about 8 |
| Ethanol | from about 20 to about 40 |
| Propane/Butane | from about 3 to about 20 |

2. The pediculicidal composition of claim 1 consisting essentially of:

| Ingredient | % w/w |
| --- | --- |
| Water, Purified | 52.373 |
| Propylene Glycol | 2.000 |
| Nonionic Emulsifying Wax | 1.500 |
| Quaternium-52 | 1.000 |
| Pyrethrins I and II | 0.665 |
| Piperonyl Butoxide | 4.233 |
| Ethanol | 26.729 |
| Propane/Butane | 11.500 |

3. The pediculicidal composition of claim 1 consisting essentially of:

| Ingredient | % w/w |
| --- | --- |
| Water, Purified | 52.373 |
| Propylene Glycol | 2.000 |
| Nonionic Emulsifying Wax | 1.500 |
| Quaternium-52 | 1.000 |
| Pyrethrins I and II | 0.346 |
| Piperonyl Butoxide | 1.870 |
| Ethanol | 30.000 |
| Propane/Butane | 5.000 |

4. A non-residual pediculicidal aerosol mousse composition consisting essentially of
   a) from about 0.1 to about 10% w/w of at least one pyrethrin pediculicidal agent;
   b) from about 70 to about 97% w/w of a quick breaking alcoholic foaming agent comprising an aliphatic alcohol, a fatty alcohol, waters and a surface active agent; and
   c) from about 3 to about 20% w/w of an aerosol propellant,
wherein said pyrethrin pediculicidal agent and said foaming agent act synergistically in the eradication of lice infestations of lice belonging to the genus Pediculus.

5. The composition of claim 4 wherein said quick breaking alcoholic foaming agent comprises:
   i) from about 20 to about 60% w/w of an aliphatic alcohol;
   ii) from about 0.5 to about 5.0% w/w of a fatty alcohol;
   iii) from about 30 to about 80% w/w of water; and
   iv) from about 0.5 to about 5.0% w/w of a surface active agent.

6. The composition of claim 4 which further comprises an emollient.

7. The composition of claim 4 wherein said pyrethrin is present in an amount of about 0.665% w/w and the piperonyl butoxide is present in an amount of about 4.4% w/w.

8. The composition of claim 4 which further comprises from about 0.2 to about 15% w/w of a synergizer for said pyrethrin pediculicidal agent.

9. The composition of claim 8 wherein said synergizer is piperonyl butoxide.

10. The composition of claim 5 wherein said quick breaking alcoholic foaming agent comprises from about 30 to about 60% w/w of said aliphatic alcohol.

11. The composition of claim 5 wherein said quick breaking alcoholic foaming agent comprises from about 25 to about 50% w/w of said aliphatic alcohol.

12. A non-residual pediculicidal aerosol mousse composition consisting essentially of
    a) from about 0.1 to about 10% w/w of at least one pyrethrin pediculicidal agent;
    b) from about 70 to about 97% w/w of a quick-breaking, alcoholic foaming agent comprising an aliphatic alcohol, a fatty alcohol, water, and a surface active agent; and
    c) from about 3 to about 20% w/w of an aerosol propellant.

13. The composition of claim 12 wherein said quick breaking alcoholic foaming agent comprises:
    i) from about 20 to about 60% w/w of an aliphatic alcohol;
    ii) from about 0.5 to about 5.0% w/w of a fatty alcohol;
    iii) from about 30 to about 80% w/w of water; and
    iv) from about 0.5 to about 50% w/w of a surface active agent.

14. The composition of claim 12 which further comprises an emollient.

15. The composition of claim 14 wherein said emollient is selected from the group consisting of glycerol, propylene glycol, sorbitol and low molecular weight polymers thereof, vinyl alcohols, polyvinyl pyrrolidone, and lanolin.

16. The composition of claim 12 which further comprises from about 0.2 to about 15% w/w of a synergizer for said pyrethrin pediculicidal agent.

17. The composition of claim 16 wherein said synergizer is piperonyl butoxide.

18. The composition of claim 13 wherein said pyrethrin is present in an amount of about 0.665% w/w and the piperonyl butoxide is present in an amount of about 4.4% w/w.

19. The composition of claim 18 wherein said pyrethrin is present in an amount of about 0.346% w/w and the piperonyl butoxide is present in an amount of about 1.87% w/w.

20. The composition of claim 18 wherein said pyrethrin is present in an amount of about 0.165% w/w and the piperonyl butoxide is present in an amount of about 1.65% w/w.

21. The composition of claim 12 wherein said aliphatic alcohol is selected from the group consisting of methyl alcohol, ethyl alcohol, isopropyl alcohol, butyl alcohol, propylene glycol and mixtures thereof, said fatty alcohol is selected from the group consisting of cetyl alcohol, stearyl alcohol, lauryl alcohol, myristyl alcohol, palmityl alcohol and mixtures thereof, said surface active agent is selected from the group consisting of ethoxylated sorbitan esters, oleates, nonyl phenol ethoxylates, fatty alcohol ethoxylates and quaternary ammonium phosphate salts, and said water is purified.

22. The composition of claim 13 wherein said quick breaking alcoholic foaming agent comprises from about 30 to about 60% w/w of said aliphatic alcohol.

23. The composition of claim 13 wherein said quick breaking alcoholic foaming agent comprises from about 25 to about 50% w/w of said aliphatic alcohol.

24. A method for killing *Pediculus humanus capitis* in humans comprising the steps of:
 (a) applying to the hair and scalp of a subject in need of such treatment a pediculicidal aerosol mousse composition of claim 12;
 (b) allowing the foam composition to remain in contact with the hair and scalp for at least about 10 minutes; and
 (c) thereafter rinsing said foam composition off the hair and scalp.

25. The method of claim 24 wherein said foaming agent comprises:
 i) from about 20 to about 60% w/w of an aliphatic alcohol;
 ii) from about 0.5 to about 50% w/w of a fatty alcohol;
 iii) from about 30 to about 80% w/w of water; and
 iv) from about 0.5 to about 5.0% w/w of surface active agent.

26. The method of claim 25 wherein said foaming agent comprises from about 30 to about 60% w/w of said aliphatic alcohol.

27. The method of claim 25 wherein said foaming agent comprises from about 25 to about 50% w/w of said aliphatic alcohol.

28. The method of claim 24 wherein said aerosol composition further comprises from about 0.2 to about 15% w/w of a synergizer for said pyrethrin pediculicidal agent.

29. The method of claim 28 wherein said synergizer is piperonyl butoxide.

* * * * *

UNITED STATES PATENT AND TRADEMARK OFFICE
CERTIFICATE OF CORRECTION

PATENT NO. : 5,783,202
DATED : July 21, 1998
INVENTOR(S) : Roderick P. Tomlinson, Neil G. Halls and Albert Z. Abram It is certified that error appears in the above-identified patent and that said Letters Patent is hereby corrected as shown below:

Column 11, line 51, "waters" should read --water--. Column 13, line 15, "50%" should read --5.0%--.

Signed and Sealed this

Seventeenth Day of November, 1998

Attest:

BRUCE LEHMAN

Attesting Officer

Commissioner of Patents and Trademarks